US006468544B1

(12) United States Patent
Egorov et al.

(10) Patent No.: US 6,468,544 B1
(45) Date of Patent: Oct. 22, 2002

(54) INTERFERON INDUCING GENETICALLY ENGINEERED ATTENUATED VIRUSES

(75) Inventors: Andrei Egorov; Thomas Muster, both of Vienna (AT); Adolfo García-Sastre, New York, NY (US); Peter Palese, Leonia, NJ (US); Sabine Brandt, Vienna (AT)

(73) Assignee: Mount Sinai School of Medicine of the City University of New York, New York, NY (US)

( * ) Notice: Subject to any disclaimer, the term of this patent is extended or adjusted under 35 U.S.C. 154(b) by 0 days.

(21) Appl. No.: 09/332,287

(22) Filed: Jun. 11, 1999

Related U.S. Application Data
(60) Provisional application No. 60/089,103, filed on Jun. 12, 1998.

(51) Int. Cl.$^7$ .................. A61K 39/145; C12N 15/63; C12N 15/66; C12N 15/86

(52) U.S. Cl. .................. 424/209.1; 424/199.1; 435/69.1; 435/320.1

(58) Field of Search ............... 435/320.1, 69.1; 424/206.1, 199.1

(56) References Cited

U.S. PATENT DOCUMENTS

| | | | |
|---|---|---|---|
| 4,071,618 A | 1/1978 | Konobe et al. | ............ 424/89 |
| 4,659,569 A | 4/1987 | Mitsuhashi et al. | ............ 424/89 |
| 5,166,057 A | 11/1992 | Palese et al. | ............ 435/69.1 |
| 5,854,037 A | 12/1998 | Palese et al. | ............ 435/172.3 |
| 5,866,694 A | 2/1999 | Katinger et al. | ............ 536/23.1 |

FOREIGN PATENT DOCUMENTS

| | | |
|---|---|---|
| EP | 0 702 085 A1 | 3/1996 |
| EP | 0 780 475 A1 B1 | 6/1997 |
| JP | 59-39831 | 3/1984 |
| WO | WO 96/34625 A1 | 11/1996 |
| WO | WO 97/06270 A1 | 2/1997 |
| WO | WO 97/12032 A1 | 4/1997 |
| WO | WO 98/02530 A1 | 1/1998 |
| WO | WO 98/13501 A2 | 4/1998 |
| WO | WO 98/53078 A1 | 11/1998 |
| WO | WO 99/02657 A1 | 1/1999 |
| WO | WO 99/15672 A1 | 4/1999 |

OTHER PUBLICATIONS

Snyder et al. Virus Res. 1990, vol. 15, pp. 69–83.*
Orkin et al. Report and recombinants of the panel to assess the NIH investimant in research on gene therapy. 1995.*
Vema et al. Nature 1997, vol. 389, pp. 239–242.*
Aoki K et al., "Differential sensitivity of two related viruses, Newcastle disease virus and Sendai virus, to interferon in mouse Had-2 cells selective inhibition of translation of NDV mRNA.", Arch Virol. 1996;141(10):1847–62.

Baez M et al., "Complete nucleotide sequence of the influenza A/PR/8/34 virus NS gene and comparison with the NS genes of the A/Udorn/72 and A/FPV/Rostock/34 strains", Nucleic Acids Res. Dec. 11, 1980;8(23):5845–58.
Beatrice et al., "Immunogenicity in mice of temperature–sensitive mutants of vesicular stomatitis virus: early appearance in bronchial secretions of an interferon–like inhibitor", J Gen Virol. 1980; 47:529–533.
Belardelli F and Gresser I, "The neglected role of type I interferon in the T–cell response: implications for its clinical use", Immunol Today. Aug. 1996;17(8):369–72.
Butterfield et al., "Vaccination for fowl plague", Am J Vet Res. Apr. 1978; 39(4):671–674.
Crowe JE, "Immune responses of infants to infection with respiratory viruses and live attenuated respiratory virus candidate vaccines", Vaccine. Aug. 1998; 16(14/15):1423–1432.
de la Luna S et al., "Influenza virus NS1 protein enhances the rate of translation initiation of viral mRNAs", J Virol. Apr. 1995;69(4):2427–33.
Desmyter J. et al., "Defectiveness of interferon production and of rubella virus interference in a line of African green monkey kidney cells (Vero)", J Virol. Oct. 1968;2(10):955–61.
Diaz MO et al., "Homozygous deletion of the alpha– and beta 1–interferon genes in human leukemia and derived cell lines", Proc Natl Acad Sci U S A. Jul. 1988;85(14):5259–63.
Durbin JE et al., "Targeted disruption of the mouse Stat1 gene results in compromised innate immunity to viral disease", Cell. Feb. 9, 1996;84(3):443–50.
Egorov et al., "Transfectant influenza A viruses with long deletions in the NS1 protein grow efficiently in Vero cells", J Virol. Aug. 1998;72(8):6437–41.
Egorov et al., "Generation of influenza A transfectant viruses containing of the carboxyl–terminal part of the NS1 protein", in *Emergence and Re–emergence of Negative Strand Viruses, Tenth International Conference on Negative Strand Viruses*. 1997, Dublin, Ireland. Abstract No. 108, p. 104.
Egorov Alu et al., "[The NS gene—a possible determinant of apathogenicity of a cold–adapted donor of attenuation A/Leningrad/134/47/57 and its reassortants]", Vopr Virusol. Sep.–Oct. 1994;39(5):201–5. Russian.

(List continued on next page.)

Primary Examiner—James Housel
Assistant Examiner—Bao Qun Li
(74) Attorney, Agent, or Firm—Pennie & Edmonds LLP (57) ABSTRACT

The present invention relates to genetically engineered attenuated viruses and methods for their production. In particular, the present invention relates to engineering live attenuated viruses which contain a modified NS gene segment. Recombinant DNA techniques can be utilized to engineer site specific mutations into one or more noncoding regions of the viral genome which result in the down-regulation of one or more viral genes. Alternatively, recombinant DNA techniques can be used to engineer a mutation, including but not limited to an insertion, deletion, or substitution of an amino acid residue(s) or an epitope(s) into a coding region of the viral genome so that altered or chimeric viral proteins are expressed by the engineered virus.

9 Claims, 6 Drawing Sheets

OTHER PUBLICATIONS

Enami M and Palese P, "High–efficiency formation of influenza virus transfectants", J Virol. May 1991;65(5):271–3.

Enami M et al., "An influenza virus containing nine different RNA segments", Virology. Nov. 1991;185(1):291–8.

Enami K et al., "Influenza virus NS1 protein stimulates translation of the M1 protein", J Virol. Mar. 1994;68(3):1432–7.

Fodor E et al., "Attenuation of influenza A virus mRNA levels by promoter mutations", J Virol. Aug. 1998;72(8):6283–90.

Fortes P et al., "Influenza virus NS1 protein inhibits pre–mRNA splicing and blocks mRNA nucleocytoplasmic transport", EMBO J. Feb. 1, 1994;13(3):704–12.

Garcia–Sastre A et al., "Influenza A virus lacking the NS1 gene replicates in interferon–deficient systems", Virology. Dec. 20, 1998;252(2):324–30.

Garcia–Sastre A et al., "The role of interferon in influenza virus tissue tropism", J Virol. Nov. 1998;72(11):8550–8.

Goodpasture et al. "The cultivation of vaccine and other viruses in the chorioallantoic membrane of chick embryos", Science. 934; 74(1919):371–372.

Haller O et al., "Genetic resistance to influenza virus in wild mice", Curr Top Microbiol Immunol. 1986;127:331–7.

Haller O et al., "Host gene influences sensitivity to interferon action selectively for influenza virus", Nature Feb. 14, 1980;283(5748):660–2.

Haller O., "Inborn resistance of ice to orthomyxoviruses", Curr Top Microbiol Immunol. 1981;92:25–52.

Hatada E et al., "Binding of influenza A virus NS1 protein to dsRNA in vitro", J Gen Virol. Dec. 1992;73 (Pt12):3325–9.

Krug and Soeiro, 1975, "Studies on the intranuclear localization of influenza virus–specific proteins", Virology 64: 378–87.

Krug, 1995, "Chapter 8. Unique Functions of the NS1 Protein" in *Textbook of Influenza* Nicholson et al. (eds.), pp. 82–92.

Li X and Palese P, "Characterization of the polyadenylation signal of influenza virus RNA", J Virol. Feb. 1994;68(2):1245–9.

Li X and Palese P, "Mutational analysis of the promoter required for influenza virus virion RNA synthesis", J Virol. Jul. 1992;66(7):4331–8.

Lu Y et al., "The influenza virus NS1 protein: a novel inhibitor of pre–mRNA splicing", Genes Dev. Aug. 1, 1994;8(15):1817–28.

Lu Y et al., "Binding of the influenza virus NS1 protein to double–stranded RNA inhibits the activation of the protein kinase that phosphorylates the elF–2 translation initiation factor", Virology. Dec. 1, 1995;214(1):222–8.

Luo GX et al., "The polyadenylation signal of influenza virus RNA involves a stretch of uridines followed by the RNA duplex of the panhandle structure", J Virol. Jun. 1991;65(6):2861–7.

Luytjes W et al., "Amplification, expression, and packaging of foreign gene by influenza virus", Cell. Dec. 22, 1989;59(6):1107–13.

Marion RM et al., "The N–terminal half of influenza virus NS1 protein is fully active both in mRNA nuclear retention and enhancement of translation", in *Emergence and Re–emergence of Negative Strand Viruses, Tenth International Conference on Negative Strand Viruses*. 1997, Dublin, Ireland. Abstract No. 240, p. 170.

Marion RM et al., "The N–terminal half of the influenza virus NS1 protein is sufficient for nuclear retention of mRNA and enhancement of viral mRNA translation", Nucleic Acids Res. Nov. 1, 1997;25(21):4271–7.

Meraz MA et al., "Targeted disruption of the Stat1 gene in mice reveals unexpected physiology specificity in the JAK–STAT signaling pathway", Cell. Feb. 9, 1996;84(3):431–42.

Mosca JD et al., "Transcriptional and posttranscriptional regulation of exogenous human beta interferon gene in simian cells defective in interferon synthesis", Mol Cell Biol. Jun. 1986;6(6):2279–83.

Murphy B.R. and R.G. Webster, 1996, "Orthomyxoviruses" in *Fields Virology*, Lippincott–Raven P.A., pp. 1397–1445.

Muster T et al., "An influenza A virus containing influenza B virus 5' and 3' noncoding regions on the neuraminidase gene is attenuated in mice", Proc Natl Acad Sci U S A. Jun 15, 1991;88(12):5177–81.

Nemeroff ME et al., "Influenza virus NS1 protein interacts with the cellular 30kDa subunit of CPSF and inhibits 3'end formation of cellular pre–mRNAs", Mol Cell. Jun. 1998;1(7):991–1000.

Nemeroff ME et al., "Unique interactions of the influenza virus NS 1 protein with host cell nuclear functions", in *Emergence and Re–emergence of Negative Strand Viruses, Tenth International Conference on Negative Strand Viruses*. 1997, Dublin, Ireland. Abstract No. 229, p. 164.

Norton GP et al., "Infectious influenza A and B virus variants with long carboxyl terminal deletions in the NS1 polypeptides", Virology. Feb. 1987;156(2):204–13.

Park YW and Katze MG, "Translational control by influenza virus. Identification of cis–acting sequences and trans–acting factors which may regulate selective viral mRNA translation", J Biol Chem. Nov. 24, 1995;270(47):28433–9.

Parvin JD et al., "Nonsense mutations affecting the lengths of the NS1 nonstructural proteins of influenza A virus isolates", Virology. Jul. 30, 1983;128(2):512–7.

Perry MM and Sang HM, "Transgenesis in chickens", Transgenic Res. May 1993;2(3):125–33.

Piccone ME et al., "Mutational analysis of the influenza virus vRNA promoter", Virus Res. May 1993;28(2):99–112.

Pleschka S et al., "A plasmid–based reverse genetics system for influenza A virus", J Virol. Jun. 1996;70(6):4188–92.

Qin XQ et al., "Interferon–beta gene therapy inhibits tumor formation and causes regression of established tumors in immune–deficient mice", Proc Natl Acad Sci U S A. Nov. 24, 1998;95(24):14411–6.

Qiu Y and Krug RM, "The influenza virus NS1 protein is a poly(A)–binding protein that inhibits nuclear export of mRNAs containing poly(A)", J Virol. Apr. 1994;68(4):2425–32.

Qiu Y et al., "The influenza virus NS1 protein binds to a specific region in human U6 snRNA and inhibits U6–U2 and U6–U4 sn RNA interactions during splicing", RNA. May 1995;1(3):304–16.

Sang H., "Transgenic chickens—methods and potential applications", Trends Biotechnol. Oct. 1994;12(10):415–20.

Sekellick MJ et al., "Interferon induction by viruses. XIV. Development of interferon inducibility and its inhibition in chick embryo cells"aged" in vitro", J Interferon Res. 1985 Fall;5(4):651–67.

Sekellick MJ et al., "Development of the interferon system. I. In chicken cells development in ovo continues on time in vitro", In Vitro Cell Dev Biol. Oct. 1990;26(10):997–1003.

Shaw et al., 1996, "Nucleocapsid protein alone is sufficient for the generation of influenza transfectants" in *Options for the Control of Influenza III*, Brown (eds.), Hampson Webster (Elsevier Science) pp. 433–436.

Shuman RM., "Production of transgenic birds", Experientia. Sep. 15, 1991;47(9):897–905.

Stern CD., "Chick stem cells", Curr Top Microbiol Immunol. 1996;212:195–206.

Tobita K et al., "Nucleotide sequence and some biological properties of the NS gene of a newly isolated influenza B virus mutant which has a long carboxyl terminal deletion in the NS1 protein", Virology. Jan. 1990;174(1):314–9.

Weaver BK et al., "Interferon regulatory factor 3 and CREB– binding protein/p300 are subunits of double–stranded RNA–activated transcription factor DRAF1", Mol Cell Biol. Mar. 1998;18(3):1359–68.

* cited by examiner-

INTERFERON INDUCING GENETICALLY ENGINEERED ATTENUATED VIRUSES

This application is entitled to and claims priority benefit to U.S. provisional application Ser. No. 60/089,103, filed on Jun. 12, 1998, the contents of which are incorporated herein by reference in its entirety.

The work reflected in this application was supported, in part, by a grant from the National Institutes of Health, and the Government may have certain rights in the invention.

1. INTRODUCTION

The present invention relates to engineering attenuated viruses by altering a non-coding region or the coding sequence of a viral nonstructural (NS) gene. In particular, the present invention relates to engineering live attenuated influenza viruses which induce interferon and related pathways. The present invention further relates to the use of the attenuated viruses and viral vectors against a broad range of pathogens and/or antigens, including tumor specific antigens. The present invention also relates to a host-restriction based selection system for the identification of genetically manipulated influenza viruses. In particular, the present invention relates to a selection system to identify influenza viruses which contain modified NS gene segments.

2. BACKGROUND OF THE INVENTION

2.1. ATTENUATED VIRUSES

Inactivated virus vaccines are prepared by "killing" the viral pathogen, e.g., by heat or formalin treatment, so that it is not capable of replication. Inactivated vaccines have limited utility because they do not provide long lasting immunity and, therefore, afford limited protection. An alternative approach for producing virus vaccines involves the use of attenuated live virus vaccines. Attenuated viruses are capable of replication but are not pathogenic, and, therefore, provide for longer lasting immunity and afford greater protection. However, the conventional methods for producing attenuated viruses involve the chance isolation of host range mutants, many of which are temperature sensitive; e.g., the virus is passaged through unnatural hosts, and progeny viruses which are immunogenic, yet not pathogenic, are selected.

Recombinant DNA technology and genetic engineering techniques, in theory, would afford a superior approach to producing an attenuated virus since specific mutations could be deliberately engineered into the viral genome. However, the genetic alterations required for attenuation of viruses are not known or predictable. In general, the attempts to use recombinant DNA technology to engineer viral vaccines have mostly been directed to the production of subunit vaccines which contain only the protein subunits of the pathogen involved in the immune response, expressed in recombinant viral vectors such as vaccinia virus or baculovirus. More recently, recombinant DNA techniques have been utilized in an attempt to produce herpes virus deletion mutants or polioviruses which mimic attenuated viruses found in nature or known host range mutants. Until very recently, the negative strand RNA viruses were not amenable to site-specific manipulation at all, and thus could not be genetically engineered.

2.2. THE INFLUENZA VIRUS

Virus families containing enveloped single-stranded RNA of the negative-sense genome are classified into groups having non-segmented genomes (Paramyxoviridae, Rhabdoviridae) or those having segmented genomes (Orthomyxoviridae, Bunyaviridae and Arenaviridae). The Orthomyxoviridae family, described in detail below, and used in the examples herein, contains only the viruses of influenza, types A, B and C.

The influenza virions consist of an internal ribonucleoprotein core (a helical nucleocapsid) containing the single-stranded RNA genome, and an outer lipoprotein envelope lined inside by a matrix protein (M). The segmented genome of influenza A consists of eight molecules (seven for influenza C) of linear, negative polarity, single-stranded RNAs which encode ten polypeptides, including: the RNA-directed RNA polymerase proteins (PB2, PB1 and PA) and nucleoprotein (NP) which form the nucleocapsid; the matrix proteins (M1, M2); two surface glycoproteins which project from the lipoprotein envelope: hemagglutinin (HA) and neuraminidase (NA); and nonstructural proteins whose function is unknown (NS1 and NS2). Transcription and replication of the genome takes place in the nucleus and assembly occurs via budding on the plasma membrane. The viruses can reassort genes during mixed infections.

Influenza virus adsorbs via HA to sialyloligosaccharides in cell membrane glycoproteins and glycolipids. Following endocytosis of the virion, a conformational change in the HA molecule occurs within the cellular endosome which facilitates membrane fusion, thus triggering uncoating. The nucleocapsid migrates to the nucleus where viral mRNA is transcribed as the essential initial event in infection. Viral mRNA is transcribed by a unique mechanism in which viral endonuclease cleaves the capped 5'-terminus from cellular heterologous mRNAs which then serve as primers for transcription of viral RNA templates by the viral transcriptase. Transcripts terminate at sites 15 to 22 bases from the ends of their templates, where oligo(U) sequences act as signals for the template-independent addition of poly(A) tracts. Of the eight viral mRNA molecules so produced, six are monocistronic messages that are translated directly into the proteins representing HA, NA, NP and the viral polymerase proteins, PB2, PB1 and PA. The other two transcripts undergo splicing, each yielding two mRNAs which are translated in different reading frames to produce M1, M2, NS1 and NS2. In other words, the eight viral mRNAs code for ten proteins: eight structural and two nonstructural. A summary of the genes of the influenza virus and their protein products is shown in Table I below.

TABLE I

INFLUENZA VIRUS GENOME RNA SEGMENTS AND CODING ASSIGNMENTS[a]

| Segment | Length[b] (Nucleotides) | Encoded Polypeptide[c] | Length[d] (Amino Acids) | Molecules Per Virion | Comments |
|---|---|---|---|---|---|
| 1 | 2341 | PB2 | 759 | 30–60 | RNA transcriptase component; host cell RNA cap binding |
| 2 | 2341 | PB1 | 757 | 30–60 | RNA transcriptase component; initiation of transcription; endonuclease activity? |

TABLE I-continued

INFLUENZA VIRUS GENOME RNA SEGMENTS AND CODING ASSIGNMENTS[a]

| Segment | Length[b] (Nucleotides) | Encoded Polypeptide[c] | Length[d] (Amino Acids) | Molecules Per Virion | Comments |
|---|---|---|---|---|---|
| 3 | 2233 | PA | 716 | 30–60 | RNA transcriptase component; elongation of mRNA chains? |
| 4 | 1778 | HA | 566 | 500 | Hemagglutinin; trimer; envelope glycoprotein; mediates attachment to cells |
| 5 | 1565 | NP | 498 | 1000 | Nucleoprotein; associated with RNA; structural component of RNA transcriptase |
| 6 | 1413 | NA | 454 | 100 | Neuraminidase; tetramer; envelope glycoprotein |
| 7 | 1027 | $M_1$ | 252 | 3000 | Matrix protein; lines inside of envelope |
|  |  | $M_2$ | 96 |  | Structural protein in plasma membrane; spliced mRNA |
|  |  | ? | ?9 |  | Unidentified protein |
| 8 | 890 | $NS_1$ | 230 |  | Nonstructural protein; function unknown |
|  |  | $NS_2$ | 121 |  | Nonstructural protein: function unknown; spliced mRNA |

[a]Adapted from R. A. Lamb and P. W. Choppin (1983), Reproduced from the Annual Review of Biochemistry, Volume 52, 467–506.
[b]For A/PR/8/34 strain
[c]Determined by biochemical and genetic approaches
[d]Determined by nucleotide sequence analysis and protein sequencing The Influenza A genome contains eight segments of single-stranded RNA of negative polarity, coding for nine structural and one nonstructural proteins. The nonsructural protein NS1 is abundant in influenza virus infected cells, but has not been detected in virions. NS1 is a phosphoprotein found in the nucleus early during infection and also in the cytoplasm at later times of the viral cycle (King et al., 1975, Virology 64: 378). Studies with temperature-sensitive (ts) influenza mutants carrying lesions in the NS gene suggested that the NS1 protein is a transcriptional and post-transcriptional regulator of mechanisms by which the virus is able to inhibit host cell gene expression and to stimulate viral protein synthesis. Like many other proteins that regulate post-transcriptional processes, the NS1 protein interacts with specific RNA sequences and structures. The NS1 protein has been reported to bind to different RNA species including: vRNA, poly-A, U6, $_{sn}$RNA, 5' untranslated region as of viral mRNAs and ds RNA (Qiu et al., 1995, Rna 1:304; Qiu et al., 1994, J. Virol. 68:2425). Expression of the NS1 protein from cDNA in transfected cells has been associated with several effects: inhibition of nucleo-cytoplasmic transport of mRNA, inhibition of pre-mRNA splicing, inhibition of host mRNA polyadenylation and stimulation of translation of viral mRNA (Fortes, et al., 1994, Embo J. 13:704; Enami, K. et al, 1994, J. Virol. 68: 1432 de la Luna, et al., 1995, J. Virol. 69:2427; Lu, Y. et al., 1994, Genes Dev. 8:1817; Park, et. al., 1995, J. Biol Chem. 270, 28433).

3. SUMMARY OF THE INVENTION

The present invention relates to genetically engineered live attenuated viruses which induce an interferon and related responses. In a preferred embodiment the present invention relates to engineering live attenuated influenza viruses which contain modified NS gene segments. The present invention also relates to both segmented and non-segmented viruses genetically engineered to have an attenuated phenotype and an interferon inducing phenotype, such a phenotype is achieved by targeting the viral gene product which interferes with the cellular interferon response. The attenuated viruses of the present invention may be engineered by altering the non-coding region of the NS gene segment that regulates transcription and/or replication of the viral gene so that it is down regulated. In non-segmented viruses, the down regulation of a viral gene can result in a decrease in the number of infectious virions produced during replication, so that the virus demonstrates attenuated characteristics. A second approach involves engineering alterations of the NS coding region so that the viral protein expressed is altered by the insertion, deletion or substitution of an amino acid residue or an epitope and an attenuated chimeric virus is produced. This approach may be applied to a number of different viruses and is advantageously used to engineer a negative strand RNA virus in which a NS gene product plays a role in regulating the interferon-mediated inhibition of translation of viral proteins.

The present invention is further related to vaccines and methods of inhibiting viral infection. The attenuated viruses of the present invention may be used to protect against viral infection. As demonstrated by the evidence presented in the Examples herein, the attenuated viruses of the present invention have anti-viral activity when administered prior to infection with wild-type virus, thus demonstrating the prophylactic utility of the attenuated viruses of the present invention.

The present invention is further related to a host-restriction based selection system for the identification of genetically manipulated influenza viruses. The selection system of the present invention is more particularly related to the identification of genetically manipulated influenza viruses which contain modified NS gene segments.

The present invention is based, in part, on the Applicants' surprising discovery that an engineered influenza A virus deleted of the NS1 gene was able to grow in a cell line deficient in type 2 IFN production, but was undetectable in Madin-Darby canine kidney (MDCK) cells and in the allantoic membrane of embryonated chicken eggs, two conventional substrates for influenza virus. The Applicants' further discovered that the infection of human cells with the engineered influenza A virus deleted of the NS1 gene, but not the wild-type virus, induced high levels of expression of genes under control of IFN-induced promoter. These results allow for the first time an efficient selection system for influenza viruses which contain NS1 mutants, where previously it was not possible to screen for viruses with an NS1 deleted phenotype.

The attenuated viruses of the invention may advantageously be used safely in live virus vaccine formulation. As used herein, the term "attenuated" virus refers to a virus which is infectious but not pathogenic; or an infectious virus which may or may not be pathogenic, but which either produces defective particles during each round of replication or produces fewer progeny virions than does the corresponding wild type virus during replication. Pathogenic viruses which are engineered to produce defective particles or a reduced number of progeny virions are "attenuated" in that even though the virus is capable of causing disease, the titers of virus obtained in a vaccinated individual will provide only subclinical levels of infection.

4. DESCRIPTION OF THE FIGURES

FIG. 1. Schematic representations of the NS genes and NS-specific mRNAs of (A) wild-type influenza A/PR/9/34 virus (WT NS) and (B) transfectant delNS1 influenza virus. Genomic RNA segments are represented as white boxes flanked by black squares. The latter represent the non coding regions of the gene. NS-specific mRNAs are also represented. Thin lines at the ends of the mRNAs represent untranslated regions. 5' cap structures (black circles) and poly(A) tails in the mRNAs are shown. The open reading frame of the NS1 protein is represented as a grey box. The specific-NEP (Nuclear Export Protein) open reading frame is shown as a hatched box. The NEP MRNA derived from the wild-type NS gene is a spliced product of the NS1 mRNA, as indicated by the V-shaped line.

FIG. 2. RT-PCR analysis of the NS RNA segment of delNS1 transfectant virus. The NS viral RNA from purified influenza A/PR/8/33 virus (wt) or from delNS1 virus (delNS1) was amplified by coupled reverse transcription-PCR using the oligonucleotide primers described in Section 6. The PCR products were run on a 2% agarose gel and stained with ethidium bromide. The positions of size markers are indicated on the right.

FIG. 3. Protein expression in delNS1 virus-infected (A) Vero cells and (B) MDCK cells. Cells were infected with delNS1 virus at an MOI of 0.02, [$^{35}$S] labeled at the indicated time points, and total amount of viral proteins was immunoprecipitated using a polyclonal antiserum against influenza virus. Immunoprecipitated products were analyzed by SDS-PAGE. The major structural viral proteins, hemagglutinin (HA), nucleoprotein (NP), neuraminidase (NA) and matrix protein (M1) are indicated by the arrows. Molecular size markers are shown on the left.

5. DETAILED DESCRIPTION OF THE INVENTION

The present invention relates to genetically engineered attenuated viruses and methods for their production. In particular, the present invention relates to engineering live attenuated viruses which contain a modified NS gene segment. Recombinant DNA techniques can be utilized to engineer site specific mutations into one or more noncoding regions of the viral genome which result in the down-regulation of one or more viral genes. Alternatively, recombinant DNA techniques can be used to engineer a mutation, including but not limited to an insertion, deletion, or substitution of an amino acid residue(s) or an epitope(s) into a coding region of the viral genome so that altered or chimeric viral proteins are expressed by the engineered virus.

The present invention further relates to a novel selection system to identify influenza viruses containing a modified NS gene segment. The selection system of the present invention is based, in part, on the host-restriction of wild-type influenza virus and the ability of influenza virus carrying a modification in the NS gene segment to infect and grow in an IFN-deficient cell.

The present invention is based, in part, on the Applicants' surprising discovery that an engineered influenza A virus deleted of the NS1 gene segment is able to grow in a cell line deficient in IFN production, but is undetectable in Madin-Darby canine Kidney (MDCK) cells and in the allantoic membrane of embryonated chicken eggs, two conventional substrates for influenza virus. The engineered influenza virus eleted of NS1 was further found by Applicants to induce IFN responses in human cells. The Applicants also found that an engineered influenza viruses deleted of NS1 is capable of replicating and inducing disease in animals that were deficient in IFN signaling, but is nonpathogenic in wild-type mice.

The present invention further relates to the use of the attenuated viruses of the present invention as a vaccine against a broad range of viruses and/or antigens, including tumor specific antigens. Many methods may be used to introduce the live attenuated virus formulations to a human or animal subject to an immune response. These include, but are not limited to, oral, intradermal, intramuscular, intraperitoneal, intravenous, subcutaneous and intranasal routes. In a preferred embodiment, the attenuated viruses of the present invention are formulated for delivery as an intranasal vaccine.

5.1. ATTENUATED VIRUSES WHICH INDUCE INTERFERON RESPONSES

The present invention relates to genetically engineered negative strand RNA viruses containing a modification, mutation, substitution, or deletion in the gene whose product is responsible for the virus bypass of the cellular interferon response. Thus, the present invention relates to genetically engineered RNA viruses, both segmented and non-segmented, containing a mutation in the gene responsible for down-regulating the cellular IFN response. The genetically engineered attenuated viruses of the present invention have an interferon-inducing phenotype, as opposed to the wild-type viruses which inhibit cellular interferon mediated responses.

In a preferred embodiment, the present invention relates to attenuated influenza viruses with a modified NS gene segment and methods of identifying those modified influenza viruses. The present invention is based, in part, on the discovery that although a NS1 modified virus is able to grow in IFN deficient cells, such as, Vero cells, its ability to replicate was severely impaired in MDCK cells and in embryonated chicken eggs. It could be possible that these growth deficiencies are due to changes in RNA segments other than the NS gene. In order to rule out this possibility, the virus was "repaired" by rescuing an engineered wild-type NS gene into the delNS1 virus. The resulting transfectant virus grew to wild-type levels in MDCK cells and in eggs, demonstrating that the lack of the NS1 gene determines the phenotypic characteristics of the delNS1 virus.

Since NS modified viruses are capable of replicating in Vero cells which are deficient in IFN expression, this indicates that altered tissue culture and egg growth of NS modified viruses is due to IFN-mediated effects. The following evidence supports the role of IFN-mediated effects: (a) The levels of viral protein expression are similar in delNS1 virus-infected Vero and in IFNαR–/– cells, but that they are markedly reduced in MDCK cells. It should be noted that IFNαR–/– cells and Vero cells are both deficient in inducing an antiviral IFN response, although the genetic defect responsible for this deficiency is different for these two cell lines. (b) Infection with the NS modified virus but not with wild-type virus induced transactivation of an IFN-stimulated reporter gene in 293 cells. (c) Finally, the delNS1 virus was able to replicate and to induce disease in mice that were deficient in IFN signaling, i.e. STAT1–/– animals, but the virus was nonpathogenic in wild-type mice.

The importance of type I IFN is illustrated by the fact that many viruses express antagonists which counteract IFN-mediated responses by the host. Examples include VA RNAs of adenoviruses, the Epstein-Barr virus-encoded structural small RNAs, the K3L and E3L gene products of vaccinia virus, the NSP3 gene product of group C rotavirus, and the reovirus σ3 protein, among others. It is interesting that several of these viral products, like the NS1 protein of influenza A virus, are able to bind to dsRNA preventing activation of PKR. Thus, the attenuated viruses of the present invention may also be used to supplement any anti-viral therapeutic in that it enhances the IFN-mediated response, a response that most viruses have developed complex mechanisms to bypass.

The attenuated influenza virus of the present invention may be used to express heterologous sequences, including viral and tumor antigens. Thus, the attenuated viruses may be used to express a wide variety of antigenic epitopes, i.e., epitopes that induce a protective immune response to any of a variety of pathogens, or antigens that bind neutralizing antibodies may be expressed by or as part of the chimeric viruses. The attenuated virus of the present invention is an excellent vehicle to introduce antigenic epitopes given that it induces an IFN-mediated response and it is not pathogenic to the host.

In accordance with the present invention, the genetic manipulation of the NS gene of influenza A viruses may help in generating viral vaccine vectors which express novel antigens and/or polypeptides. Since the NS RNA segment is the shortest among the eight viral RNAs, it is possible that the NS RNA will tolerate longer insertions of heterologous sequences than other viral RNAs. Moreover, the NS RNA segment directs the synthesis of high levels of protein in infected cells, suggesting that it would be an ideal segment for insertions of foreign antigens. However, in accordance with the present invention any one of the eight segments of influenza may be used for the insertion of heterologous sequences.

Heterologous gene coding sequences flanked by the complement of the viral polymerase binding site/promoter, e.g., the complement of 3'-influenza virus terminus, or the complements of both the 3'- and 5'-influenza virus termini may be constructed using techniques known in the art. Recombinant.DNA molecules containing these hybrid sequences can be cloned and transcribed by a DNA-directed RNA polymerase, such as bacteriophage T7, T3 or the Sp6 polymerase and the like, to produce the recombinant RNA templates which possess the appropriate viral sequences that allow for viral polymerase recognition and activity.

One approach for constructing these hybrid molecules is to insert the heterologous coding sequence into a DNA complement of an influenza virus genomic segment so that the heterologous sequence is flanked by the viral sequences required for viral polymerase activity; i.e., the viral polymerase binding site/promoter, hereinafter referred to as the viral polymerase binding site. In an alternative approach, oligonucleotides encoding the viral polymerase binding site, eq., the complement of the 3'-terminus or both termini of the virus genomic segments can be ligated to the heterologous coding sequence to construct the hybrid molecule. The placement of a foreign gene or segment of a foreign gene within a target sequence was formerly dictated by the presence of appropriate restriction enzyme sites within the target sequence. However, recent advances in molecular biology have lessened this problem greatly. Restriction enzyme sites can readily be placed anywhere within a target sequence through the use of site-directed mutagenesis (e.g., see, for example, the techniques described by Kunkel, 1985, Proc. Natl. Acad. Sci. U.S.A. 82; 488). Variations in polymerase chain reaction (PCR) technology, described infra, also allow for the specific insertion of sequences (i.e., restriction enzyme sites) and allow for the facile construction of hybrid molecules. Alternatively, PCR reactions could be used to prepare recombinant templates without the need-of cloning. For example, PCR reactions could be used to prepare double-stranded DNA molecules containing a DNA-directed RNA polymerase promoter (eq., bacteriophage T3, T7 or Sp6) and the hybrid sequence containing the heterologous gene and the influenza viral polymerase binding site. RNA templates could then be transcribed directly from this recombinant DNA. In yet another embodiment, the recombinant RNA templates may be prepared by ligating RNAs specifying the negative polarity of the heterologous gene and the viral polymerase binding site using an RNA ligase. Sequence requirements for viral polymerase activity and constructs which may be used in accordance with the invention are described in the subsections below.

5.2. GENERATION OF ATTENUATED VIRUSES

The present invention relates to genetically engineered attenuated viruses, and methods for their production. In particular, the invention relates to attenuated influenza viruses which have been modified in such a way to result in an IFN-independent and IFN-inducing phenotype. The following section describes the various approaches which may be used in accordance with the invention to generate an attenuated phenotype. Recombinant DNA techniques can be utilized to engineer site specific mutations into one or more noncoding regions of the viral genome which result in the down-regulation of one or more viral gene. Alternatively, recombinant DNA techniques can be used to engineer a mutation, including but not limited to an insertion, deletion, or substitution of an amino acid residue(s) or an epitope(s) into a coding region of the viral genome so that altered or chimeric viral proteins are expressed by the engineered virus. The invention is based, in part, on the discovery that the down regulation of a viral gene in segmented viruses results in the production of defective particles at each round of replication, so that the virus demonstrates attenuated characteristics. In non-segmented viruses, the down-regulation of a viral gene may result in the production of fewer progeny virions than would be generated by the corresponding wild type virus. The alterations of the viral proteins described also result in attenuation for reasons which are less well understood.

Many methods may be used to introduce the live attenuated virus formulations to a human or animal subject to induce an immune response; these include, but are not limited to, oral, intradermal, intramuscular, intraperitoneal, intravenous, subcutaneous and intranasal routes. It is preferable to introduce the chimeric virus vaccine via its natural route of infection.

Any virus may be engineered in accordance with the invention to produce an attenuated strain suitable for use as a safe live-virus vaccine, including but not limited to viruses belonging to the families set forth in Table I below.

TABLE I

FAMILIES OF HUMAN AND ANIMAL VIRUSES

| VIRUS CHARACTERISTICS | VIRUS FAMILY |
|---|---|
| dsDNA | |
| Enveloped | Poxviridae |
| | Irididoviridae |
| | Herpesviridae |
| Nonenveloped | Adenoviridae |
| | Papovaviridae |
| | Hepadnaviridae |
| ssDNA | |
| Nonenveloped | Parvoviridae |
| dsRNA | |
| Nonenveloped | Reoviridae |
| | Birnaviridae |
| ssRNA | |
| Enveloped | |
| Positive-Sense Genome | |
| No DNA Step in Replication | Togaviridae |
| | Flaviviridae |
| | Coronaviridae |
| | Hepatitis C Virus |
| DNA Step in Replication | Retroviridae |

TABLE I-continued

FAMILIES OF HUMAN AND ANIMAL VIRUSES

| VIRUS CHARACTERISTICS | VIRUS FAMILY |
|---|---|
| Negative-Sense Genome | |
| Non-Segmented Genome | Paramyxoviridae |
| | Rhabdoviridae |
| | Filoviridae |
| Segmented Genome | Orthomyxoviridae |
| | Bunyaviridae |
| | Arenaviridae |
| Nonenveloped | Picomaviridae |
| | Calciviridae |

Abbreviations used: ds = double stranded; ss = single stranded; enveloped = possessing an outer lipid bilayer derived from the host cell membrane; positive-sense genome = for RNA viruses, genomes that are composed of nucleotide sequences that are directly translated on ribosomes, = for DNA viruses, genomes that are composed of nucleotide sequences that are the same as the mRNA; negative-sense genome = genomes that are composed of nucleotide sequencescomplementary to the positive-sense strand.

DNA viruses (e.g., vaccinia, adenoviruses, baculovirus) and positive strand RNA viruses (e.g., poliovirus) may be readily engineered using recombinant DNA techniques which are well known in the art (e.g., see U.S. Pat. No. 4,769,330 to Paoletti; U.S. Pat. No. 4,215,051 to Smith; Racaniello et al., 1981, Science 214: 916–919). Until recently, however, negative strand RNA viruses (e.g., influenza) were not amenable to site specific genetic manipulation because the viral RNAs are not infectious. However, a recently developed technique, called "reverse genetics," allows the engineering and production of recombinant negative strand RNA viruses.

The reverse genetics technique involves the preparation of synthetic recombinant viral RNAs that contain the non-coding regions of the negative strand virus which are essential for the recognition of viral RNA by viral polymerases and for packaging signals necessary to generate a mature virion. The recombinant RNAs are synthesized from a recombinant DNA template and reconstituted in vitro with purified viral polymerase complex to form recombinant ribonucleoproteins (RNPs) which can be used to transfect cells. A more efficient transfection is achieved if the viral polymerase proteins are present during in vitro transcription of the synthetic RNAs. The synthetic recombinant RNPs can be rescued into infectious virus particles. The foregoing techniques are described in U.S. Pat. No. 5,166,057, issued Nov. 24, 1992 and in Enami & Palese, 1991, J. Virol. 65:2711–2713, each of which is incorporated by reference herein in its entirety), and influenza A viruses containing insertions, deletions and mutations with the stalk portion of the NS gene, which changes acts as a host range mutant.

5.2.1. DOWN-REGULATION OF VIRAL GENES

In accordance with the invention, a non-coding regulatory region of a virus can be altered to down-regulate a viral gene involved in down-regulating the cellular IFN-mediated response, e.g. reduce transcription of its mRNA and/or reduce replication of vRNA (viral RNA), so that an attenuated virus with an IFN-inducing phenotype is produced.

This approach, while applicable to any virus, is particularly attractive for engineering viruses with segmented genomes; i.e., viruses in which the genome is divided into segments that are packaged into virions. For example, the segmented genome of influenza A virus (an orthomyxovirus) consists of eight molecules of linear negative-sense ssRNAs which encode ten polypeptides, including: the RNA-directed RNA polymerase proteins (PB2, PB1 and PA) and nucleoprotein (NP) which form the nucleocapsid; two surface glycoproteins which project from the envelope: hemagglutinin (HA) and neuraminidase (NA); and nonstructural proteins (NS1 and NS2) whose function is unknown. The termini of each segment contain the non-coding regions essential for recognition by viral polymerase and for packaging signals necessary to generate a mature virion. The sequence of the termini is highly conserved among all eight segments. As another example, the segmented genome of reoviruses consists of 10 to 12 segments of linear dsRNA which encode 6 to 10 major structural polypeptides, a transcriptase and other enzymes.

The foregoing approach is equally applicable to non-segmented RNA viruses, where the down regulation of transcription of a viral gene involved in down-regulating the cellular IFN-mediated response, such that it will reduce the production of its mRNA and the encoded gene product and result in an interferon-inducing phenotype.

Any alteration of the regulatory non-coding regions which decrease their efficiency or strength may be engineered in accordance in the invention. For example, the strength of viral promoters can be reduced by alterations in the stem structure. In order to achieve an attenuated phenotype the cis elements of a virus gene involved in down-regulating the cellular IFN-mediated-response may be mutated to achieve a dramatic effect on transcription and replication of the gene.

How influenza A virus packages its eight RNA genome segments remains an interesting question. In the past, two different mechanisms were proposed for the packaging of influenza virus RNAs: one suggests that the eight RNAs are selectively packaged and the other that viral RNAs are packaged randomly (Compans et al., 1970, In The Biology Of Large RNA Viruses, Barry & Mahy, Eds., pp. 87–108, Academic Press, N.Y.; Lamb & Choppin, 1983, Ann. Rev. Biochem. 467–506; Smith & Hay, 1982, Virology 118:96–108). Evidence is now accumulating to support the random packaging mechanism. The random packaging theory originated from the fact that influenza viruses have a low ratio of infectious particles to physical particles. If one assumes that an average of 11 RNAs are packaged per virion, the expected ratio is compatible with that found in vivo (Enami et al., 1991, Virology 185:291–298). This model was also supported by the finding of a reassortant virus which contained two copies of the same segment derived from two different viruses (Scholtissek, 1978, Virology 89:506–516), and further support for this theory came from a more recent report which described an influenza A virus which required nine RNAs in order to be infectious (Enami et al., 1991, Virology 185: 291–298).

In summary, an attenuated phenotype may be achieved by targeting the cis elements of the NS gene segment to result in down regulation of the gene segment. Since the proteins of this virus are unaltered as compared to wild type virus, attenuation must be the result of inefficient cis-acting signals. This principal of attenuation may be applied analogously to other viruses with segmented genomes. For example, the introduction of modifications into the noncoding sequences of rotavirus genes or of genes of other segmented dsRNA viruses (Roner et al., 1990, Virology 179;845–852) should also allow the pathogenicity of these viruses to be altered.

5.2.2. ALTERATION OF VIRAL PROTEINS

An alternative way to engineer attenuated viruses involves the introduction of an alteration, including but not limited to an insertion, deletion or substitution of one or more amino acid residues and/or epitopes into one or more of the viral proteins involved in down-regulating the cellular IFN-mediated response. This may be readily accomplished by engineering the appropriate alteration into the corresponding viral gene sequence. Any change that alters the activity of the viral protein involved in down-regulating the cellular IFN-mediated response so that viral replication is modified or reduced may be accomplished in accordance with the invention.

For example, alterations that interfere with but do not completely abolish viral attachment to host cell receptors and ensuing infection can be engineered into viral surface antigens or viral proteases involved in processing to produce an attenuated strain. According to this embodiment, viral surface antigens can be modified to contain insertions, substitution or deletions of one or more amino acids or epitopes that interfere with or reduce the binding affinity of the viral antigen for the host cell receptors. This approach offers an added advantage in that a chimeric virus which expresses a foreign epitope may be produced which also demonstrates attenuated characteristics. Such viruses are ideal candidates for use as live recombinant vaccines. For example, heterologous gene sequences that can be engineered into the chimeric viruses of the invention include, but are not limited to, epitopes of human immunodeficiency virus (HIV) such as gp120; hepatitis B virus surface antigen (HBsAg); the glycoproteins of herpes virus (e.g., gD, gE); VP1 of poliovirus; and antigenic determinants of nonviral pathogens such as bacteria and parasites to name but a few.

In this regard, influenza is an ideal system in which to engineer foreign epitopes, because the ability to select from thousands of influenza virus variants for constructing chimeric viruses obviates the problem of host resistance or immune tolerance encountered when using other virus vectors such as vaccinia. In addition, since influenza stimulates a vigorous secretory and cytotoxic T cell response, the presentation of foreign epitopes in the influenza background may also provide for the secretory immunity and cell-mediated immunity. By way of example, the insertion, deletion or substitution of amino acid residues in the HA protein of influenza can be engineered to produce an attenuated strain. In this regard, alterations to the B region or E region of HA may be utilized. In accordance with this approach, the malarial epitope (ME 1) of *Plasmodium yoelii* (NEDSYVPSAEQI) was introduced into the antigenic site E of the hemagglutinin of influenza. The resulting chimeric virus has a 500- to 1,000-fold lower $LD_{50}$ (lethal dose 50) than that of wild type virus when assayed in mice. In another embodiment, the major antigenic determinant of poliovirus type 1, i.e., the BC loop of the VP1 of poliovirus type 1 (PASTTNKDKL) was engineered into the B region of the influenza HA protein. This chimeric virus is also attenuated.

In another embodiment, alterations of viral proteases required for processing viral proteins can be engineered to produce attenuation. Alterations which affect enzyme activity and render the enzyme less efficient in processing, should affect viral infectivity, packaging, and/or release to produce an attenuated virus. For example, alterations to the NS protein of influenza can be engineered to reduce NS enzyme activity and decrease the number and/or infectivity of progeny virus released during replication.

In another embodiment, viral enzymes involved in viral replication and transcription of viral genes, e.g., viral polymerases, replicases, helicases, etc. may be altered so that the enzyme is less efficient or active. Reduction in such enzyme activity may result in the production of fewer progeny genomes and/or viral transcripts so that fewer infectious particles are produced during replication.

The alterations engineered into any of the viral enzymes include but are not limited to insertions, deletions and substitutions in the amino acid sequence of the active site of the molecule. For example, the binding site of the enzyme could be altered so that its binding affinity for substrate is reduced, and as a result, the enzyme is less specific and/or efficient. For example, a target of choice is the viral polymerase complex since temperature sensitive mutations exist in all polymerase proteins. Thus, changes introduced into the amino acid positions associated with such temperature sensitivity can be engineered into the viral polymerase gene so that an attenuated strain is produced.

5.3. HOST-RESTRICTION BASED SELECTION SYSTEM

The present invention relates to a host-restriction based selection system for the identification of genetically manipulated influenza viruses. The selection system of the present invention is more particularly related to the identification of genetically manipulated influenza viruses which contain modified NS gene segments. The selection system of the present invention allows for the screening of the genetically engineered influenza viruses to identify those viruses with a modified NS gene segment.

The selection system of the present invention is based, in part, on the Applicants' discovery that an engineered influenza A virus deleted of the NS1 gene was able to grow in a cell line deficient in IFN production, whereas the same cell line would not support infection and growth of wild type influenza virus. The NS1 deleted virus was unable to infect and grow in the conventional substrates for influenza virus. Thus, the invention provides a very simple and easy screen to identify those genetically engineered influenza viruses that contain a modified NS1 gene.

5.4. VACCINE FORMULATIONS USING THE CHIMERIC VIRUSES

Virtually any heterologous gene sequence may be constructed into the chimeric viruses of the invention for use in vaccines. Preferably, epitopes that induce a protective immune response to any of a variety of pathogens, or antigens that bind neutralizing antibodies may be expressed by or as part of the chimeric viruses. For example, heterologous gene sequences that can be constructed into the chimeric viruses of the invention for use in vaccines include but are not limited to epitopes of human immunodeficiency virus (HIV) such as gp120; hepatitis B virus surface antigen (HBsAg); the glycoproteins of herpes virus (e.g. gD, gE); VP1 of poliovirus; antigenic determinants of-non-viral pathogens such as bacteria and parasites, to name but a few. In another embodiment, all or portions of immunoglobulin genes may be expressed. For example, variable regions of anti-idiotypic immunoglobulins that mimic such epitopes may be constructed into the chimeric viruses of the invention.

Either a live recombinant viral vaccine or an inactivated recombinant viral vaccine can be formulated. A live vaccine may be preferred because multiplication in the host leads to a prolonged stimulus of similar kind and magnitude to that occurring in natural infections, and therefore, confers substantial, long-lasting immunity. Production of such live recombinant virus vaccine formulations may be accomplished using conventional methods involving propagation of the virus in cell culture or in the allantois of the chick embryo followed by purification.

In this regard, the use of genetically engineered influenza virus (vectors) for vaccine purposes may require the presence of attenuation characteristics in these strains. Current live virus vaccine candidates for use in humans are either cold adapted, temperature sensitive, or passaged so that they derive several (six) genes from avian viruses, which results in attenuation. The introduction of appropriate mutations (e.g., deletions) into the templates used for transfection may provide the novel viruses with attenuation characteristics. For example, specific missense mutations which are associated with temperature sensitivity or cold adaption can be made into deletion mutations. These mutations should be more stable than the point mutations associated with cold or temperature sensitive mutants and reversion frequencies should be extremely low.

Alternatively, chimeric viruses with "suicide" characteristics may be constructed. Such viruses would go through only one or a few rounds of replication in the host. For example, cleavage of the HA is necessary to allow for reinitiation of replication. Therefore, changes in the HA cleavage site may produce a virus that replicates in an appropriate cell system but not in the human host.

When used as a vaccine, the recombinant virus would go through a single replication cycle and induce a sufficient level of immune response but it would not go further in the human host and cause disease. Recombinant viruses lacking one or more of the essential influenza virus genes would not be able to undergo successive rounds of replication. Such defective viruses can be produced by co-transfecting reconstituted RNPs lacking a specific gene(s) into cell lines which permanently express this gene(s). Viruses lacking an essential gene(s) will be replicated in these cell lines but when administered to the human host will not be able to complete a round of replication. Such preparations may transcribe and translate—in this abortive cycle—a sufficient number of genes to induce an immune response. Alternatively, larger quantities of the strains could be administered, so that these preparations serve as inactivated (killed) virus vaccines. For inactivated vaccines, it is preferred that the heterologous gene product be expressed as a viral component, so that the gene product is associated with the virion. The advantage of such preparations is that they contain native proteins and do not undergo inactivation by treatment with formalin or other agents used in the manufacturing of killed virus vaccines.

In another embodiment of this aspect of the invention, inactivated vaccine formulations may be prepared using conventional techniques to "kill" the chimeric viruses. Inactivated vaccines are "dead" in the sense that their infectivity has been destroyed. Ideally, the infectivity of the virus is destroyed without affecting its immunogenicity. In order to prepare inactivated vaccines, the chimeric virus may be grown in cell culture or in the allantois of the chick embryo, purified by zonal ultracentrifugation, inactivated by formaldehyde or β-propiolactone, and pooled. The resulting vaccine is usually inoculated intramuscularly.

Inactivated viruses may be formulated with a suitable adjuvant in order to enhance the immunological response. Such adjuvants may include but are not limited to mineral gels, e.g., aluminum hydroxide; surface active substances such as lysolecithin, pluronic polyols, polyanions; peptides; oil emulsions; and potentially useful human adjuvants such as BCG and Corynebacterium parvum.

Many methods may be used to introduce the vaccine formulations described above, these include but are not limited to oral, intradermal, intramuscular, intraperitoneal, intravenous, subcutaneous, and intranasal routes. It may be preferable to introduce the chimeric virus vaccine formulation via the natural route of infection of the pathogen for which the vaccine is designed. Where a live chimeric virus vaccine preparation is used, it may be preferable to introduce the formulation via the natural route of infection for influenza virus. The ability of influenza virus to induce a vigorous secretory and cellular immune response can be used advantageously. For example, infection of the respiratory tract by chimeric influenza viruses may induce a strong secretory immune response, for example in the urogenital system, with concomitant protection against a particular disease causing agent.

6. MATERIALS AND METHODS

The following materials and methods were used in the following Sections 7 through 11.

Viruses and cells. Influenza A/PR/8/34 (PR8) virus was propagated in 10-day-oldembryonated chicken eggs at 37° C. Influenza A virus 25A-1, a reassortant virus containing the NS segment form the cold-adapted strain A/Leningrad/ 134/47/57 and the remaining genes from PR8 virus (Egorov et al., 1994, Vopr. Virusol. 39:201–205; Shaw et al., 1996, in Options for the control of influenza III, eds. Brown, Hampson Webster (Elsevier Science) pp. 433–436) was grown in Vero cells at 34° C. The 25A-1 virus is ts in mammalian cells, and was used as helper virus for-the rescue of the delNS1 transfectant virus. Vero cells and MDCK cells in minimal essential medium (MEM) containing 1 μg/ml of trypsin (Difco Laboratories, Detroit, Mich.) were used for influenza virus growth. Vero cells were also used for selection, plaque purification and titration of the delNS1 virus. MDCK cells, 293 cells and mouse embryo fibroblasts (MEF) derived from 14–16 day embryos of IFNαR−/− mice were maintained in DMEM (Dulbecco's minimal essential medium) containing 10% heat-inactivated detal calf serum. Immortalized IFNαR−/− fibroblasts were derived from MEF by continuous passage (Todaro et al., 1963, J. Cell. Biol. 17:299–313). Vero cells were grown in AIM-V medium (Life Technologies, Grand Island, N.Y.).

Mice. C57BL/6 mice homozygous for a targeted deletion of STAT1 were generated as previously described (Durbin et al., 1996, Cell 84:443–450). IFNαR−/− mice have also been described (Hwang et al., 1995, Proc. Natl. Aced. Sci. USA 92:11284–11288). Specific pathogen free C57BL/6 and BALB/c (wild type) mice were purchased from Taconic Farms.

Animal infections. Female mice were used for influenza virus infection at 6 to 12 weeks of age. Intranasal (i.n.) inoculations were performed in wild type and STAT1−/− mice under ether anesthesia using 50 μl of MEM containing $5 \times 10^4$ plaque forming units (pfu) of delNS1 virus. Animals were monitored daily, and sacrificed when observed in extremis. All procedures were in accord with NIH guidelines on care and use of laboratory animals.

Plasmids. pT3delNS1 was made as follows. First, pPUC19-T3/NS PR8, containing the complete NS gene of PR8 virus flanked by the T3 RNA polymerase promoter and BpuAI restriction site was amplified by inverse PCR (Ochman et. al., 1988, Genetics 120:621–623) using primers 5'-CTGAAAGCTTGACACAGTGTTTG-3' and 5'-GACATACTGCTGAGGATGTC-3+ (CODON Genetic Systems, Weiden, Austria). The obtained cDNA thus lacking the NS1 gene was phosphorylated, Klenow treated, self-ligated and propagated in *E. coli* strain TG1. The construct obtained after purification was named pT3delNS1 and verified by sequencing. Plasmids for expression of the NP, PB1, PB2, and PA proteins of PR8 virus (pHMG-NP, pHMG-PB1, pHMG-PB2, and PHMG-PA) were previously described (Pleschka et al., 1996, J. Virol. 70:4188–4192). PPOLI-NS-RB was made by substituting the CAT open reading frame of pPOLI-CAT-RT (Pleschka et al., 1996, J. Virol. 70:4188–4192) within RT-PCR product derived from the coding region of the NS gene of influenza A/WSN/33 (WSN) virus. This plasmid expresses the NS-specific viral RNA segment of WSN virus under the control of a truncated human polymerase I promoter. pHISG54-1-CAT (Bluyssen et al., 1994, Eur. J. Biochem. 220:395–402) encodes the CAT reporter gene under the transcriptional control of the IFNα-stimulated promoter of the ISG-54K gene.

Generation of transfectant viruses. Generation of delNS1 virus was performed by ribonucleoprotein (RNP) transfection (Luytijes et al., 1989, Cell 59:1107–1113). The RNPs were formed by T3 RNA polymerase transcription from pT3delNS1 linearized with BpuAI in the presence of purified nucleoprotein and polymerase of influenza 25A-1 virus (Enami et al., 1991, J. Virol 65:2711–2713). RNP complexes were transfected into Vero cells which were previously infected with 25A-1 virus. Transfected cells were incubated for 18 hours at 37° C., and the supernatant was passaged twice in Vero cells at 40° C. and plaque purified three times in Vero cells covered with agar overlay media at 37° C. The isolated delNS1 virus was analyzed by RT-PCR using primers 5'-GGCCTCTAGATAATACGACTC-ACTATAAGCAAAAGCAGGGTGACAAAG-3' (complementary to position 1 to 21 at the 3' noncoding end of the NS gene) and 5'-GATCGCCTTCTATTAGTAGAAA-CAAGGGTGTTTTTATTAAATAAGCTG-3' (containing the last 38 nucleotides of the 5' noncoding end of the NS gene). NS/WSN transfectant virus was generated as follows. Vero cells in 35-mm dishes were transfected with plasmids pHMG-NP, pHMG-PB1, pHMG-PB2, PHMG-PA and pPOLI-NS-RB, as previously described (Pleschka et al., 1996, J. Virol. 70:4188–4192). 2 days postransfection, cells were infected with $5 \times 10^4$ pfu of delNS1 virus and incubated 2 more days at 37° C. Cell supernatant was passaged once in MDCK cells and twice in chicken embryonated eggs. Transfectant viruses were cloned by limiting dilution in eggs. Genomic RNA from purified NS/WSN transfectant virus was analyzed by polyacrylamide gel electrophoresis, as previously described (Zheng et al., 1996, Virology 217:242–251).

Analysis of virus protein synthesis in infected cells. Cell monolayers in 35-mm dishes were infected with $2 \times 10^4$ pfu of delNS1 virus. At intervals postinfection, cells were labeled with L-[$^{35}$S]cysteine and L-[$^{35}$S]methionine for the indicated times. Labeled cells were lysed in 10 mM tris-HCl (pH 7.4) containing 150 mM NaCl, 5 mM EDTA, 1 mM PMSF, 10% glycerol, 1% Triton X-100, 1% sodium deoxycholate and 0.1% sodium dodecylsufate (SDS). Proteins were immunoprecipitated using a rabbit polyclonal anti-influenza virus serum. Immunoprecipated proteins were analyzed by SDS-10% polyacrylamide gel electrophoresis (SDS-PAGE).

CAT transfections. 293 cell monolayers in 35-mm dishes were transfected with 1 μg of pHISG54-1-CAT using DOTAP lipofection reagent (Boehringer Mannheim) according to the manufacturer's instructions, and incubated at 37° C. 1 day postransfection cells were infected with delNS1 virus or PR8 virus at the indicated multiplicities of infection (MOI). As controls, cells were mock-infected or transfected with 50 μg of poly(I-C). After 1 day more at 37° C., cell extracts were made and assayed for CAT activity, as described (Percy et al., 1994, J. Virol. 68:4486–4492).

7. EXAMPLE

GENERATION OF THE TRANSFECTANT INFLUENZA VIRUS delNS1, LACKING THE NS1 GENE

Figure 1A:
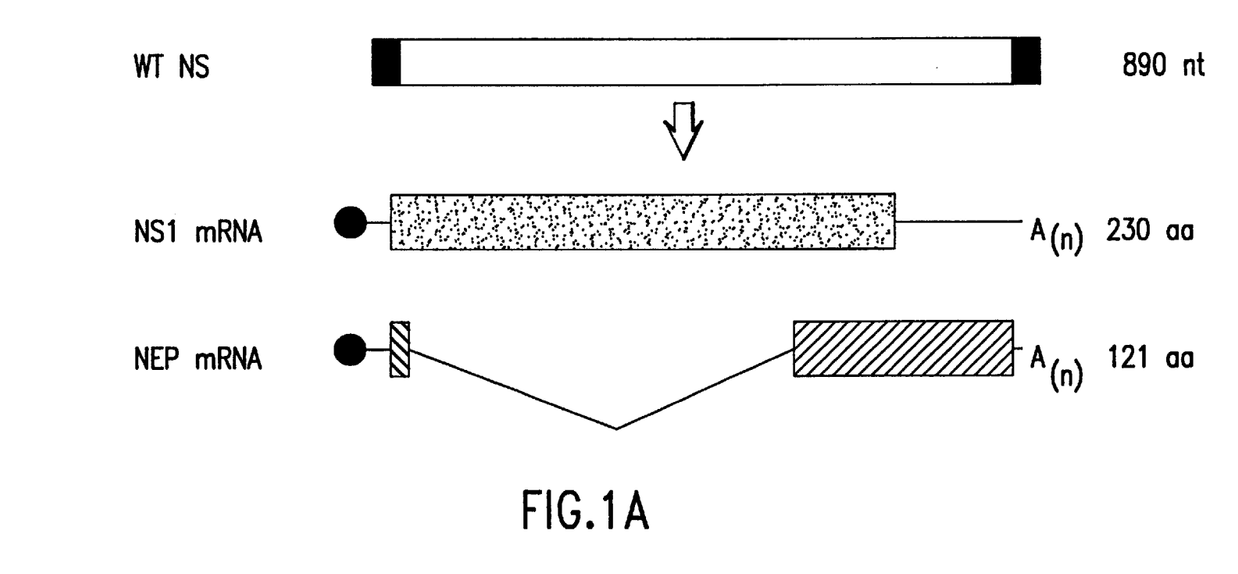
Figure 1B:
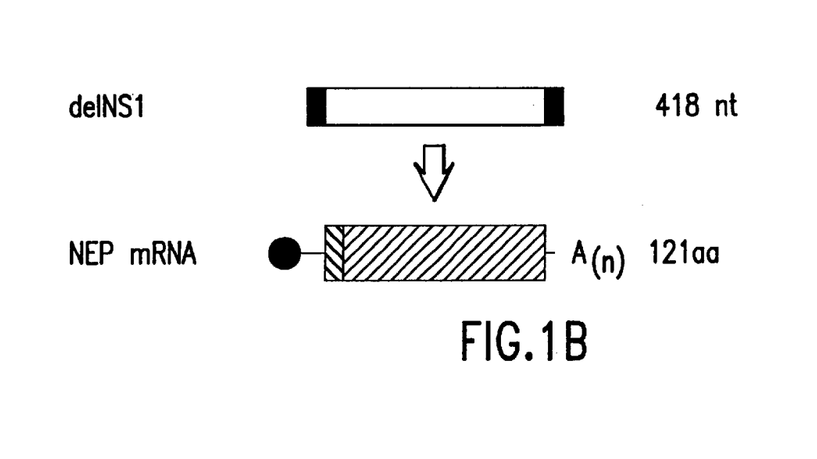
Figure 2:
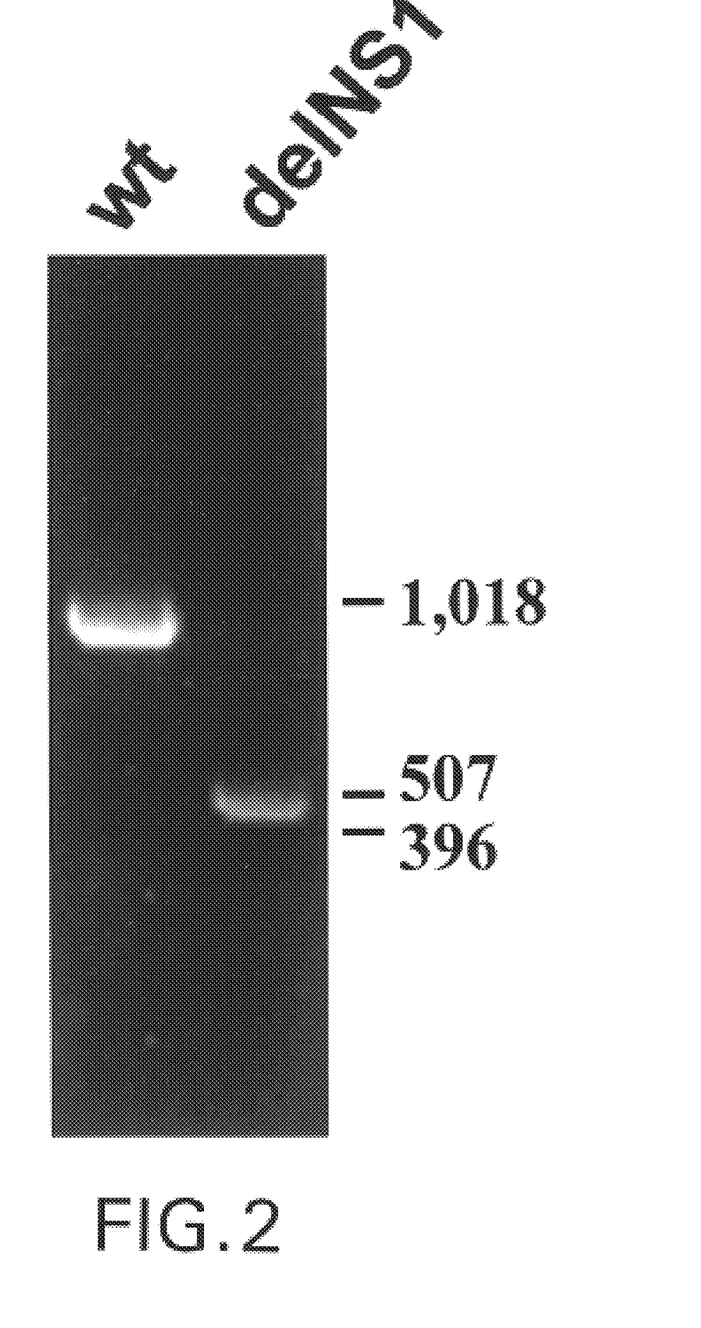
Figure 3A:
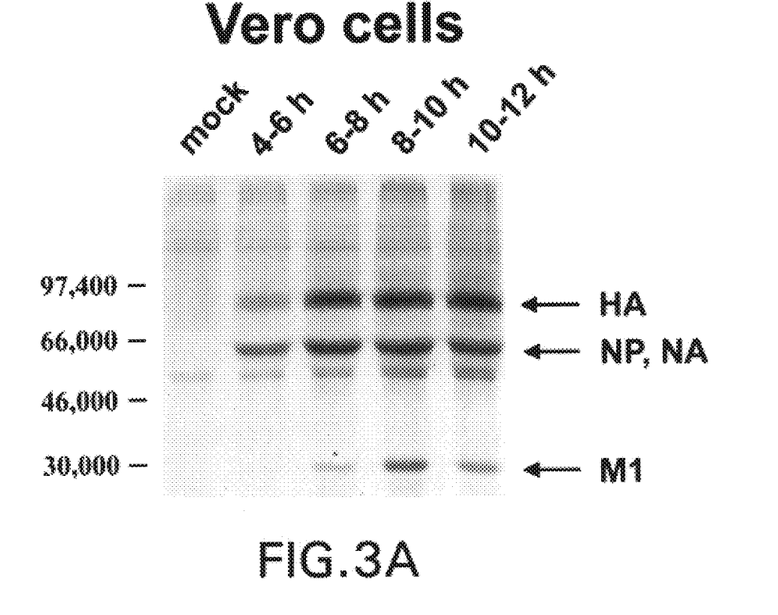
Figure 3B:
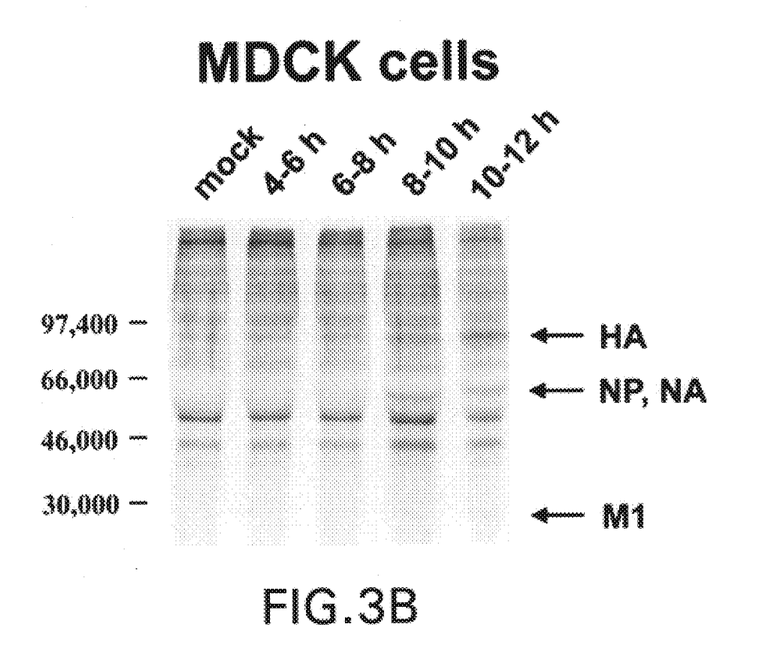
Figure 4:
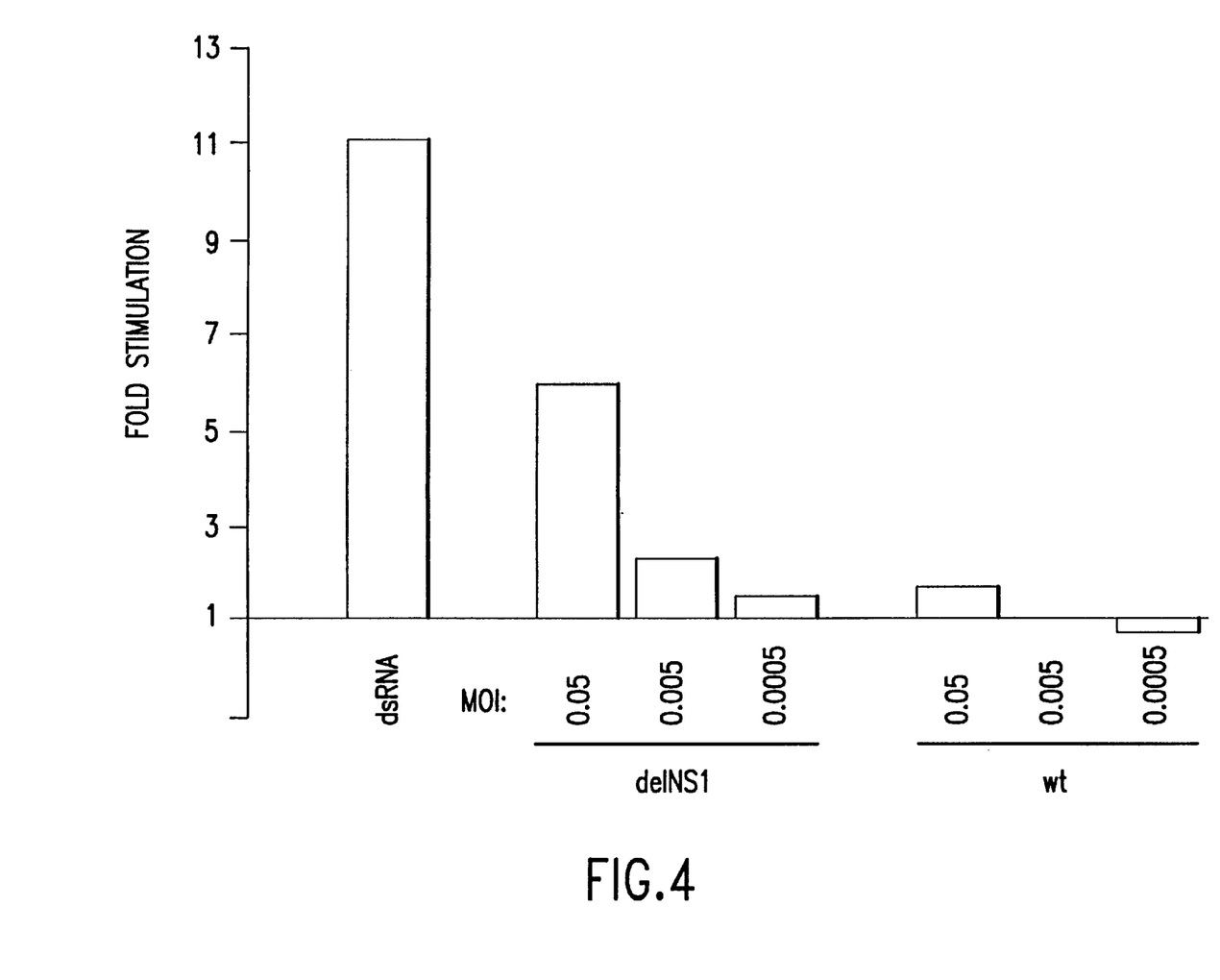
FIG. 4. Protein expression in delNS1 virus-infected IFNαR−/− cells. Cells were infected with delNS1 virus at an MOI of 0.02, and [$^{35}$S] labeled at the indicated time points. As a control, delNS1 virus-infected Vero cells were labeled in the same experiment from 8 to 10 h postinfection. Total amount of viral proteins was immunoprecipitated using a polyclonal antiserum against influenza virus. Immunoprecipitated products were analyzed by SDS-PAGE. The major structural viral proteins, hemagglutinin (HA), nucleoprotein (NP), neuraminidase.(NA) and matrix protein (M1) are indicated by the arrows. Molecular size markers are shown on the left.
Figure 5:
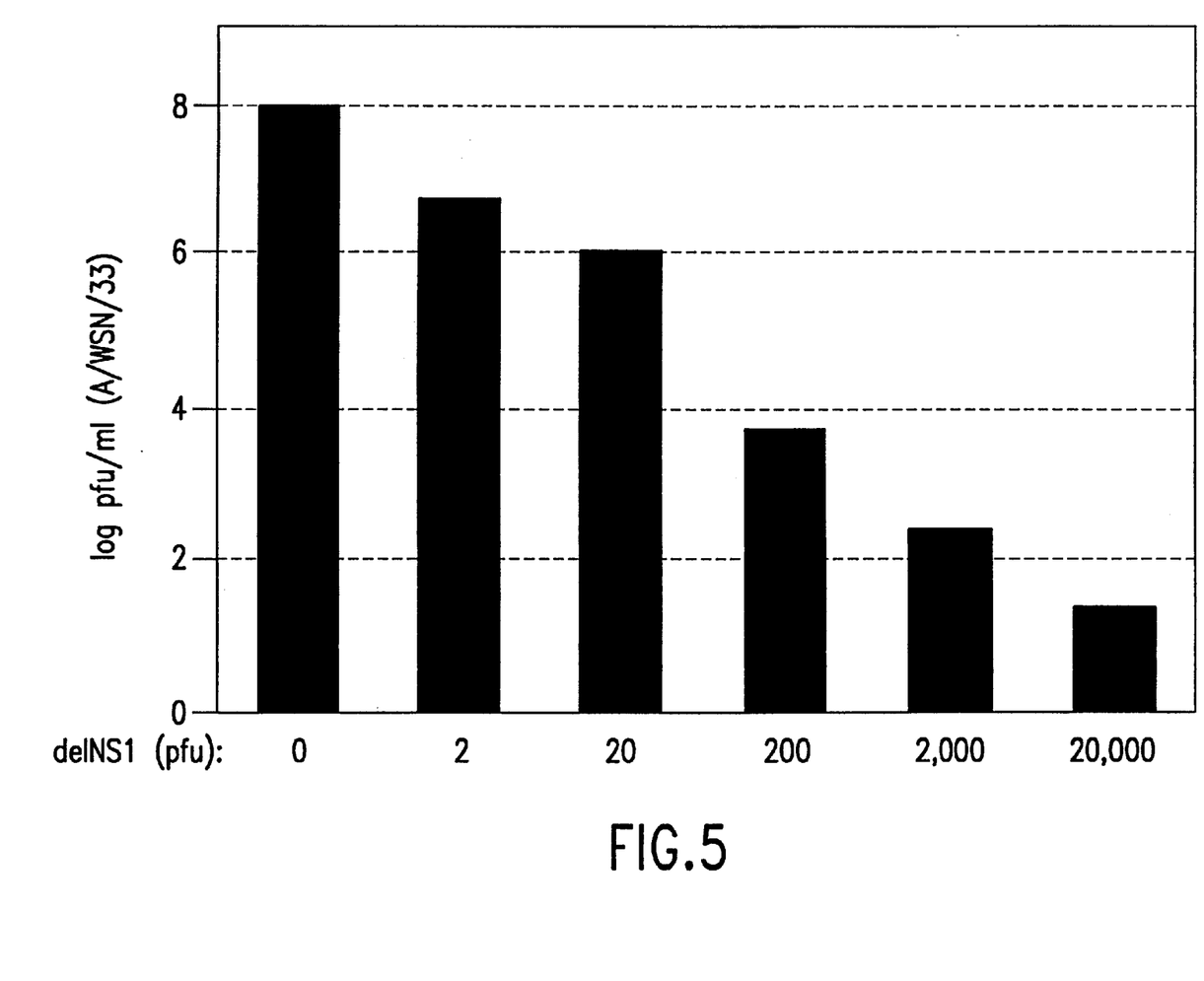
FIG. 5. Induction of transcription from an IFN-stimulated promoter by infection with delNS1 virus. 293 cells were transfected with plasmid pHISG54-1-CAT encoding the reporter gene CAT under the control of a type I IFN-stimulated promoter. One day posttransfection, cells were transfected with 50 μg of dsRNA, or infected with delNS1 virus or with wild-type influenza A/PR/8/34 virus (wt) at the indicated MOIs. One day postinfection, CAT activity was determined in cell extracts. The stimulation of CAT activity following the different treatments is indicated.

The NS-specific viral RNA segment of influenza A virus encodes both the NS1 and NEP (nuclear export protein)

proteins. Unspliced NS-specific mRNA translates into the NS1 protein, while the spliced RNA directs the synthesis of the NEP. The plasmid pT3delNS1 was constructed which expresses a mutated NS gene from influenza PR8 virus. This mutated RNA segment contains a deletion of the NS1-specific open reading frame (nt positions 57 to 528 of the PR8 NS gene (Baez et al., 1980, Nucleic Acids Res. 8:5845–5858) and thus it encodes only the NEP (FIG. 1). RNP transfection of the delNS1 gene using the ts 25A-1 helper virus yielded a progeny virus which was able to grow at 40° C. in Vero cells. Amplification of the NS gene of the rescued virus by RT-PCR confirmed the substitution of the NS gene of the helper virus with that derived from the transfected delNS1 gene (FIG. 2).

8. EXAMPLE

GROWTH PROPERTIES OF delNS1 VIRUS IN TISSUE CULTURE AND EGGS

The growth properties of delNS1 virus and wild-type PR8 virus were compared in Vero cells, MDCK cells, and 10-day-old embryonated chicken eggs. Cell monolayers containing approximately $10^6$ Vero or MDCK cells were infected with delNS1 virus or PR8 virus at an MOI of approximately 0.0005. After 4 days incubation at 37° C. using MEM containing 1 µg/ml of trypsin, supernatants were used in a hemagglutination assay. Alternatively, the allantoic cavity of 10-day-old embryonated chicken eggs was injected with $10^4$ pfu of delNS1 or PR8 virus, and the hemagglutination titer in the allantoic fluids was determined after 3 days of incubation of 37° C. As shown in Table 2, delNS1 virus was able to grow in Vero cells to titers of 16 as compared to a tier of 128 for wild-type PR8 virus. However, delNS1 virus replication was severely impaired in MDCK cells and in eggs (hemagglutination titers were undetectable in these samples).

TABLE 2

DelNS1 virus replication in tissue culture cells and eggs

| Culture media | Hemagglutination titer[1] delNS1 | WT PR8[2] |
|---|---|---|
| Vero cells | 16 | 128 |
| MDCK cells | <2 | 512 |
| Eggs | <2 | 2,048 |

[1]Titers represent the highest dilution with hemagglutinating activity
[2]Wild type influenza A/PR/8/34 virus

8.1. DELETION OF THE NS1 GENE IS RESPONSIBLE FOR THE GROWTH PROPERTIES OF delNS1.

In order to prove that the impaired viral growth of delNS1 virus in MDCK cells and eggs was due to the deletion of the NS1 gene and not to possible differences in other RNA segments of delNS1 and PR8 viruses, we used delNS1 virus as helper virus to rescue a wild-type NS gene. Transfections were carried as described in Materials and Methods using a plasmid-based expression system (Pleschka et al., 1996, J. Virol. 70:4188–4192) for the wild-type NS gene of influenza A/WSN/34 virus. Selection of transfectant NS/WSN viruses were done by serial passages in MDCK cells and eggs. SDS-PAGE analyses of purified viral RNA from NS/WSN virus confirmed the wild-type length of its NS RNA segment. Transfectant NS/WSN virus containing the NS RNA segment derived from WSN virus and the remaining segments from delNS1 (PR8) virus was able to grow to identical titers than those of wild-type PR8 virus in MDCK cells and 10-day-old embryonated chicken eggs.

8.2. VIRAL PROTEIN EXPRESSION LEVELS IN delNS1 VIRUS-INFECTED MDCK AND VERO CELLS In order to investigate if the deficiency of delNS1 virus replication MDCK cells correlated with a decrease in the expression levels of viral proteins, [$^{35}$S]-labeling experiments were performed. MDCK or Vero cells were infected with delNS1 virus at an MOI of 0.02 and labeled with L-[$^{35}$S]cysteine and L-[$^{35}$S]methionine for the indicated times. After labeling, viral proteins were immunoprecipitated from cell extracts and separated by PAGE (FIG. 3). Quantitation of the $^{35}$S signal indicates that approximately 20-fold less viral protein was synthesized by infected MDCK cells.

8.3. DelNS1 VIRUS-INFECTED VERO AND IFNαR–/– CELLS HAVE SIMILAR LEVELS OF VIRAL PROTEIN EXPRESSION

The reason for the differences between Vero and MDCK cells in supporting delNS1 virus replication and viral protein expression may relate to the inability of Vero cells to synthesize IFN (Desmyter et al., 1968, J. Virol. 2:955–961; Mosca et al., 1986, Mol. Cell. Biol. 6:2279–2283; Diaz et al., 1988, Proc. NeH. Acad. Sci. USA 85:52595263). In order to test this hypothesis, the pattern of viral protein expression was investigated in a murine cell line which is unable to respond to IFN. IFNαR knock-out cells were. infected with delNS1 virus at an MOI of 0.02 and labeled as described above. As a control, delNS1 virus-infected Vero cells were labeled from 8 to 10 hours postinfection at the same time. Levels of viral protein expression were similar in both cell lines (FIG. 4), suggesting that delNS1 virus is able to replicate in IFN-deficient systems. It should be noted that we could not investigate multicycle replication of delNS1 virus in IFNαR–/– cells because these cells die rapidly in the presence of trypsin, which is required for viral hemagglutinin activation and virus infectivity.

9. EXAMPLE

DELTA NS1 VIRUS IS A POTENT INDUCER OF INTERFERON RESPONSES

Stimulation of transcription from an IFN-regulated promoter by infection with transfectant delNS1 virus. In order to investigate if the deletion of the NS1 gene in delNS1 virus results in an enhanced IFN response in infected cells we performed transfection experiments using pHISG54-1-CAT. This plasmid contains the CAT reporter gene in front of the IFNα-stimulated promoter of the ISG-54K gene (Bluyssen et al., 1994, Eur. J. Biochem. 220:395–402). 293 cells were transfected with pHISG54-1-CAT and infected with delNS1 virus or wild-type PRB at the indicated MOIs as described in Material and Methods. CAT activity in the infected cell extracts was compared with that in uninfected cell extracts. As positive control, transcription from the IFN-regulated promoter was stimulated using poly(I-C). As shown in FIG. 5, infection at an MOI of 0.05 with delNS1 virus, but not with wild-type virus, induced approximately a 6-fold stimulation of reporter gene expression. The transfectant virus lacking the NS1 gene was thus impaired in its ability to inhibit the IFN response in 293 infected cells.

10. EXAMPLE

PATHOGENICITY OF DELTA NS1 VIRUS

Transfectant delNS1 virus is pathogenic in STAT1–/– mice. The ability of delNS1 virus to replicate and cause disease in wild-type mice and in mice deficient in the IFN responses was investigated. For this purpose, 5×$10^4$ pfu of delNS1 virus was used to i.n. infect three C57BL/6 mutant mice which were homozygous for a targeted deletion of STAT1, a transactivator which is required for the IFN signaling (Durbin et al., 1996, Cell 84:443–450; Merez et al., 1996, Cell 84:431–442). Three to four wild-type C57BL/6 and BALB/c mice were also inoculated with delNS1 virus. Infected-STAT1−/− mice looked sick by day 3 postinfection. By day 7 postinfection, all three infected STAT1−/− mice died (Table 3). DelNS1 virus was recovered from the lungs of STAT1−/− dying mice, indicating that the virus was replicating in these animals. However, all wild-type infected mice survived infection with delNS1 without developing any symptoms of disease (Table 3).

TABLE 3

Survival of mice following delNS1 virus infection[1]

| Mice | Day postinfection | | |
|---|---|---|---|
| | 1 day | 7 day | 14 day |
| STAT1−/− C57BL/6 | 3 of 3 | 0 of 3 | 0 of 3 |
| Wild-type C57BL/6 | 3 of 3 | 3 of 3 | 3 of 3 |
| Wild-type BALB/c | 4 of 4 | 4 of 4 | 4 of 4 |

[1]Mice under ether anesthesia were inoculated intranasally with $5 \times 10^4$ pfu of delNS1 virus

11. EXAMPLE

PREINOCULATION WITH delNS1 VIRUS INHIBITS REPLICATION OF INFLUENZA

In order to investigate if preinoculation with the delNS1 virus has an inhibitory effect on infection or replication of wild-type influenza, the following experiment was conducted.

Figure 6:
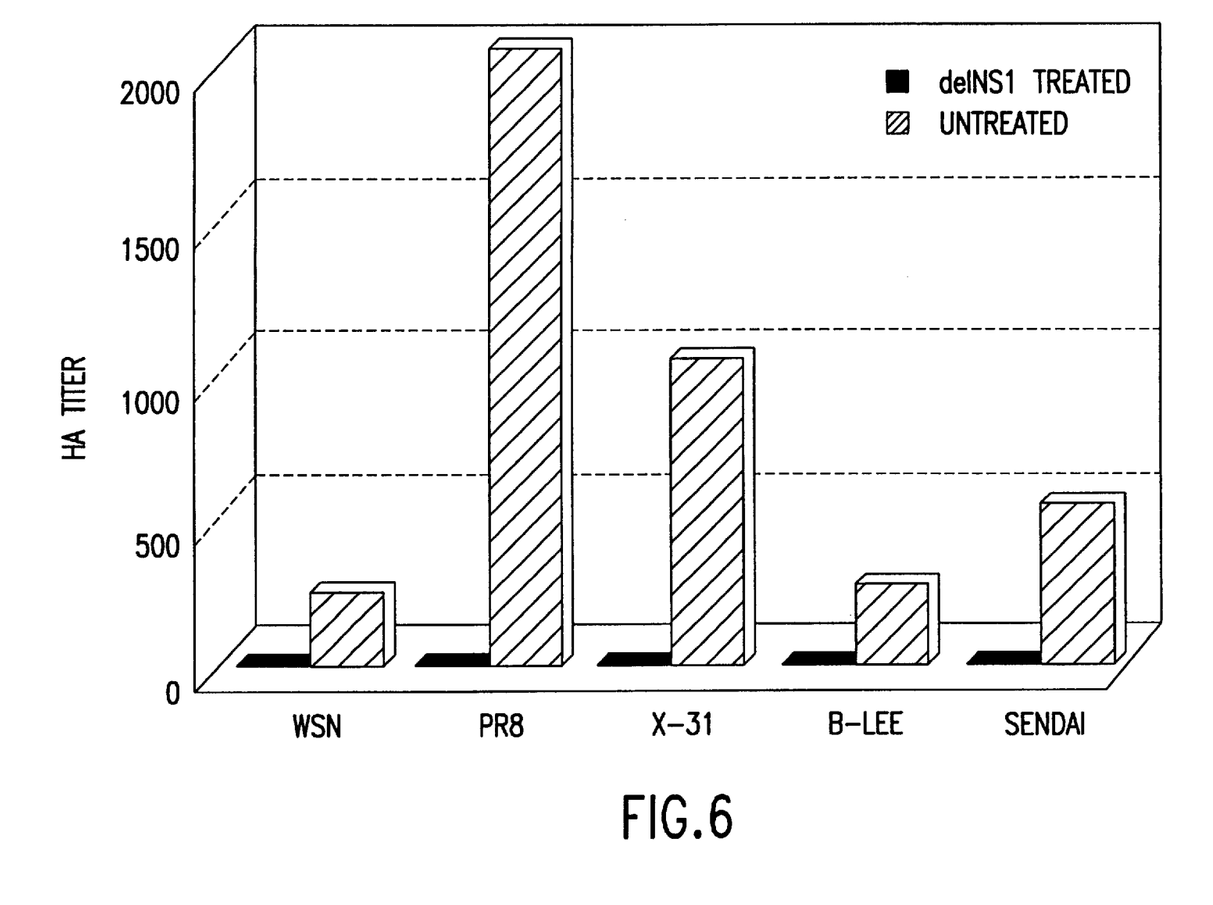
FIG. 6. Induction of antiviral response in embryonated eggs by delNS1 virus. 10-day old embryonated chicken eggs were inoculated with 20,000 plaque forming units of delNS1 virus or with PBS (untreated). After 8 h incubation at 37° C., the eggs were reinfected with $10^3$ pfu of H1N1 influenza A/WSN/33 virus (WSN), H1N1 influenza A/PR/8 virus (PR8), H3N2 influenza A/X-31 virus (X-31), influenza B/Lee/40 virus (B-Lee), or Sendai virus (Sendai). B-Lee infected eggs were incubated at 35° C. for additional 40 h. All other eggs were incubated at 37° C. for additional 40 h. Virus present in the allantoic fluid was titrated by hemagglutination assay.

In this study 10-day old embroyated chicken eggs were inoculated with 20,000 pfu of the delNS1 virus or with PBS into the allantoic cavity. After 8 hours of incubation at 37° C., the eggs were reinfected with $10^3$ pfu of H1N1 influenza A/WSN/33 (WSN); H1N1 influenza A/PR/8 virus (PR8), H3N2 influenza A/X-31 virus (X-31), influenza B/Lee/40 virus (B-Lee) or Sendai virus and incubated for an additional 40 hours at 37° C., except for B-Lee infected cells which were incubated at 35° C. As shown in FIG. 6, the delNS1 virus treated eggs resulted in undetectable levels of viral infection, when compared to the untreated cells. Thus, demonstrating the anti-viral activity of the delNS1 virus and its potential as an anti-viral therapeutic and prophylactic.

The present invention is not to be limited in scope by the specific embodiments described which are intended as single illustrations of individual aspects of the invention, and any constructs or viruses which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

Various references are cited herein, the disclosures of which are incorporated by reference in their entireties.

What is claimed is:

1. An attenuated genetically engineered influenza A virus with an interferon-inducing phenotype wherein said virus comprises a viral genome wherein the complete NS1 coding sequences have been deleted (delNS1).

2. An attenuated genetically engineered influenza A virus which is infectious and replicates in an interferon (IFN) deficient cell line, wherein said virus comprises a viral genome wherein the complete NS1 coding sequences have been deleted (delNS1).

3. The attenuated virus of claim 1 or 2 which further encodes a heterologous sequence.

4. The attenuated virus of claim 1 or 2 in which the heterologous sequence encodes a viral antigenic peptide.

5. The attenuated virus of claim 1 or 2 in which the heterologous sequence encodes a tumor antigenic peptide.

6. The attenuated virus of claim 3, wherein the heterologous sequence is derived from a bacteria, virus, or parasite.

7. An immunogenic composition comprising an influenza A virus deINS1, in a suitable pharmaceutical composition.

8. The composition of claim 7 which is formulated for intranasal delivery.

9. The method of inducing an immune response comprising administering to a subject the composition of claim 7.

* * * * *